United States Patent [19]
Sonderegger

[11] Patent Number: 5,643,628
[45] Date of Patent: Jul. 1, 1997

[54] SUTURE TIPPING APPARATUS AND METHOD

[75] Inventor: Marcel Sonderegger, Schaffhausen, Switzerland

[73] Assignee: United States Surgical Corporation, Norwalk, Conn.

[21] Appl. No.: 460,962

[22] Filed: Jun. 5, 1995

[51] Int. Cl.$^6$ .................. A61L 17/00; B05D 1/28; B05D 3/00
[52] U.S. Cl. .................. 427/2.31; 427/175; 427/293; 427/356; 427/398.1; 427/429
[58] Field of Search .................. 427/2.31, 172, 427/286, 288, 175, 2.29, 429, 355, 356, 293, 398.1

[56] References Cited

U.S. PATENT DOCUMENTS

| | | |
|---|---|---|
| 2,513,432 | 7/1950 | Sisson .................. 427/434.6 |
| 2,734,506 | 2/1956 | Nichols et al. . |
| 3,736,646 | 6/1973 | Schmitt et al. . |
| 3,849,185 | 11/1974 | Shepherd et al. . |
| 3,890,975 | 6/1975 | McGregor . |
| 3,930,059 | 12/1975 | Wells .................. 427/2.29 |
| 3,941,897 | 3/1976 | Vecchia .................. 427/11 |
| 3,980,177 | 9/1976 | McGregor .................. 206/63.3 |
| 4,020,194 | 4/1977 | McIntyre et al. .................. 427/172 |
| 4,054,144 | 10/1977 | Hoffman et al. .................. 128/339 |
| 4,060,885 | 12/1977 | Hoffman et al. .................. 29/407 |
| 4,277,301 | 7/1981 | McIntyre et al. .................. 427/288 |
| 4,285,907 | 8/1981 | Hugemann et al. .................. 422/100 |
| 4,551,516 | 11/1985 | Kitamura .................. 528/18 |
| 4,687,827 | 8/1987 | Russo .................. 427/429 |
| 4,722,384 | 2/1988 | Matsutani .................. 163/1 |
| 4,799,311 | 1/1989 | Matsutani .................. 29/209 |
| 4,922,904 | 5/1990 | Uetake et al. .................. 606/226 |
| 5,046,350 | 9/1991 | Proto et al. .................. 72/416 |
| 5,099,676 | 3/1992 | Proto et al. .................. 72/416 |
| 5,102,418 | 4/1992 | Granger et al. .................. 427/255.6 |
| 5,269,808 | 12/1993 | Proto et al. .................. 606/228 |
| 5,350,373 | 9/1994 | Colligan .................. 606/1 |
| 5,382,455 | 1/1995 | Boockmann .................. 427/11 |
| 5,452,517 | 9/1995 | Lothmann .................. 427/286 |
| 5,507,777 | 4/1996 | Kus et al. .................. 427/2.1 |

*Primary Examiner*—Diana Dudash

[57] ABSTRACT

A process for tipping surgical sutures includes dispensing tipping agent one drop at a time and contacting the suture portion to be tipped with the drop of tipping agent. A transversely oriented lifting/wiping string may be used to lift the suture into contact with the drop and may wipe away excess tipping agent. Alternatively, a transversely oriented string may be used to catch a drop and then place the drop onto the suture. The tipping agent absorbed into the tipped portion can then be cured and cut to provide a tipped suture. The tipping process and apparatus can be used in conjunction with a needle-suture assembly process. The process advantageously controls application of a droplet of tipping agent to minimize the amount of tipping agent used, thereby providing an aesthetic needle-suture attachment. Apparatus are disclosed for performing the process.

27 Claims, 8 Drawing Sheets

FIG_2

FIG_3

FIG_4

FIG_10

FIG_11

SUTURE TIPPING APPARATUS AND METHOD

BACKGROUND

1. Technical Field

The present apparatus and method relate to the tipping of surgical sutures with tipping agent to stiffen a portion of the suture prior to cutting.

2. Background of the Art

Tipping of surgical sutures is known in the art and is generally performed to prevent the brooming of a multifilament surgical suture when cut so that it may be more easily inserted into the shank end of a surgical needle.

For many years, surgeons have employed needle suture combinations in which a suture or ligature is attached to the shank end of a needle. Such needle suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acid.

One typical method for securing a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114.

Insertion of sutures into a hole, recess or tube for attachment to surgical needles presents problems peculiar to suture needle combinations. Braided multifilament sutures in particular are difficult to insert into the very small aperture of a surgical needle; unless modified, they are too limp for the suture tip to be controlled for insertion and they have a tendency to "broom", i.e, the filaments have a tendency to flare out at the cut end so that the diameter of the cut end exceeds the diameter of the needle hole. Various techniques have been employed to modify sutures to overcome the problems of limpness and brooming. One known method employs a tipping agent, which is a material used to coat the suture to stiffen the filaments and adhere them together.

Typically, a suture to be tipped is first placed under tension to reduce slack so that the suture may be maintained in a predetermined position on a frame or rack or other suture holding device. Optionally, the tension may be such as to reduce the diameter of the suture. See Canadian Patent No. 1,009,532. The suture is then dipped into the tipping solution and allowed to dry while under tension. The sutures are then dried, such as by being warmed in a drying oven at about 225° F. for about 10 minutes. After drying the sutures can be cut and released from tension. The process results in a tipped end on each side of a cut. Where tension has optionally been employed to reduce the suture diameter, release of said tension will allow the suture to expand to its original diameter except at the tipped end portion. This can facilitate insertion of the end into a needle.

Tipping agents may be dissolved in solvents to form dipping solutions. By way of example, Mariotte mixture is a dipping solution comprising nylon dissolved in isopropyl alcohol. Other polymers and solvents may also be used. Gould mixture is a dipping solution comprising nylon dissolved in methanol. At least one major manufacturer of surgical needles recommends use of Mariotte mixture or Gould mixture for tipping sutures. A multitude of other tipping agents, including polymers and solvents, have been proposed. For example McGregor U.S. Pat. No. 3,890,975 discloses coating the suture with a binding resin or adhesive. The composition may be any non-toxic adhesive composition, either organic, inorganic or a hybrid. Suitable organic materials are such natural products as starch, dextrin, asphalt, animal and vegetable proteins, natural rubber, shellac, semi-synthetic products such as cellulose nitrate and the other cellulosies, polyamides derived from dimer acids, castor-oil based polyurethanes; such well-known synthetic resins as vinyl-type addition polymers, both resins and elastomers; polyvinyl acetate, polyvinyl alcohol, acrylics, unsaturated polyesters, butadiene/acrylonitrile, butadiene/styrene, neoprene, butyl rubber, polyisobutylene; and polymers formed by condensation and other step-wise mechanisms, i.e., epoxies, polyurethanes, polysulfide rubbers, and the reaction products of formaldehyde with phenol, resorcinol, urea, and melamine. McGregor states that particularly preferred bonding compositions are epoxide resins and polyester resins.

Schmitt U.S. Pat. No. 3,736,646 discloses that it is known to tip braided sutures by dipping the end of the suture in a plastic such as a solution in isopropyl alcohol. Schmitt suggest that for absorbable sutures an absorbable tipping agent is desirable, and proposes that a copolymer of lactic and glycolic acid dissolved in a suitable organic solvent, such as xylene or toluene, be applied to tip the suture.

Nichols U.S. Pat. No. 2,734,506 discloses a dipping solution of polymers of methacrylic acid esters in an organic solvent such as toluene, xylene acetone, ethyl acetate, methylethyl ketone, or naphtha.

Shepherd et al. U.S. Pat. No. 3,849,185 discloses the use of an acrylic casing syrup as a tipping agent, the syrup being fully polymerized after being applied to the suture.

In addition, paraffin/hexane solution (10% paraffin has been used as a suture coating agent as well as Arrochem (TM), a nylon resin plus methanol composition manufactured by Arrochem, Inc. of 201 Westland Farm Road, Mr. Holly, N.C. 28120, and SILASTIC (TM) Medical Adhesive (a silicon elastomer composition manufactured by Dow Corning Co.)

An improved method of tipping sutures is disclosed and described in U.S Pat. No. 5,269,808, which is herein incorporated by reference in its entirety. In this method cyanoacrylate monomer is used as the tipping agent. The suture portion to be tipped is passed through a mist of cyanoacrylate which has been generated by an ultrasonically powered nozzle. The cyanoacrylate hardens very rapidly after being absorbed into the braided suture and adheres the filaments so that the filaments will not broom when the tipped portion is cut. One of the advantages of this method is that the cyanoacrylate works very well on sutures which have previously been coated and/or filled with lubricants, and/or therapeutic agents and the like.

While the spray application of cyanoacrylate has been effective for tipping sutures there is yet a need to apply the cyanoacrylate or other tipping agent more efficiently. In particular, it would be desirable to minimize the length of suture tipped so that little, if any, of the tipped portion extends out of the needle shank after needle-suture attachment.

SUMMARY

A method and apparatus for tipping a suture are provided herein. The method includes the steps of drawing a multifilament surgical suture under tension from a suture supply, dispensing one or more drops of liquid tipping agent of predetermined size, contacting a portion of the suture with the drop(s), and permitting the tipping agent to be absorbed into the suture to create a tipped portion of the suture.

An optional elongated member oriented transverse to the linear orientation of the suture may be provided in order to lift the suture into contact with the drop. The elongated member is preferably an absorbent string which can also be used to wipe excess tipping agent from the tipped portion of the suture.

The tipping agent is cured by a means suitable to the type of tipping agent being used and the suture is then cut to create a tipped end, which is then inserted into the barrel end of a needle.

Also contemplated is the use of non-absorbent strings to catch a droplet of tipping agent from the dispenser and carry the drop to the suture, which then absorbs the drop.

Alternatively, a suture twisting feature may be included to rotate the suture to insure even exposure of the suture portion and coverage by tipping agent.

BRIEF DESCRIPTION OF THE DRAWINGS

Various embodiments are described with reference to the drawings wherein.

DETAILED DESCRIPTION OF THE PREFERRED EMBODIMENT(S)

The following applications are incorporated by reference in their entirety: U.S. application Ser. No. 08/309,705, now U.S. Pat. No. 5,540,778 filed Sep. 21, 1994 directed to a method and apparatus for tipping, cutting, and sorting sutures; and U.S. application Ser. No. 08/297,202 filed Aug. 29, 1994, now abandoned, directed to a method and apparatus for micro-needle suture attachment.

As used herein, the term "braid" means a strand formed by crossing a number (at least three) of individual yarns composed of one or more filaments diagonally in such manners that each strand passes alternatively over and under one or more of the others. The terms "top", "bottom", "above", "below", "over", "under", "distal", "proximal", "forward", "rearward" and their variants, are used relative to each other and do not refer to any external fixed frame of reference.

Overview of Process

The process described herein achieves tipping of surgical sutures in an efficient manner while providing a superior product. Less tipping agent is required and the length of suture which is tipped can be regulated such that only that portion of the suture inserted into the needle is stiffened. The remainder of the suture, which is exposed to the body tissue, advantageously remains limp.

1. The Suture Supply

The suture to be tipped is drawn off a supply spool under tension, the amount of tension preferably being sufficient to reduce the suture diameter by tightening the filaments.

Tipping processes are applied to multifilament surgical sutures, especially braided multifilament sutures. The braid may be of traditional tubular braid construction or spiroid braid construction and may include a core section composed of one or more filaments around which the braid is externally fabricated. Suitable braid constructions are disclosed, for example, in U.S. Pat. Nos. 5,261,886; 5,059,213; 5,019,093; 3,565,077; and 3,187,752.

The suture can be fabricated from a wide variety of natural and synthetic fibrous materials. Such materials include non-absorbable as well as partially and fully bio-absorbable (i.e., resorbable) natural and synthetic fiber-forming polymers. Non-absorbable materials which are suitable for fabricating sutures include silk, polyamides, polyesters such as polyethylene and polypropylene, silk, cotton, linen, etc. Bio-absorbable sutures may be fabricated from natural collagenous material or synthetic resins including those derived from glycolic acid, glycolide, lactic acid, lactide, dioxanone, polycaprolactone, epsiloncaprolactone, trimethylene carbonate, etc., and various combinations of these and related monomers. Sutures prepared from resins of this type are known in the art. See, e.g., U.S. Pat. Nos. 3,297,033; 3,839,297; and 4,429,080.

Braided multifilament sutures typically are coated with one or more coating compositions to improve functional properties such as surface lubricity and knot tie-down behavior. A variety of suture coating compositions proposed for either or both of these purposes are well known in the art, e.g., those disclosed in U.S. Pat. Nos. 3,867,190; 3,942,532; 4,047,533; 4,452,973; 4,624,256; 4,649,920; 4,716,203; 4,826,945, 4,994,074; 5,123,912, and 5,312,437.

Absorbable braided sutures may also contain a storage stabilizing amount of a filler material containing at least one water soluble liquid polyhydroxy compound and/or ester thereof. Such filling compositions are disclosed in U.S. Pat. Nos. 5,051,272 and 5,037,429. Moreover, since the polyhydroxy compounds are generally capable of dissolving a variety of medico-surgically useful substances, such as therapeutic agents, these compounds can be used as vehicles to deliver such substances to a wound or surgical site at the time the suture is introduced into the body.

As stated, a braided suture may be impregnated with one or more medico-surgically useful substances, e.g., those which accelerate or beneficially modify the healing process when the suture is applied to a wound or surgical site. So, for example, the braided suture herein can be provided with a therapeutic agent which will be deposited at the sutured site. For example, a therapeutic agent can be chosen for its antimicrobial properties, capability for promoting wound repair and/or tissue growth or for specific indications such as thrombosis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a surgical or trauma wound site. To promote wound repair and/or tissue growth, one or more biologically active materials known to achieve either or both of these objectives can be applied to a braided suture. Such materials include any of several Human Growth Factors (HGFs), magainin, tissue or kidney plasminogen activator to cause thrombosis, superoxide dismutase to scavenge tissue damaging free radicals, tumor necrosis factor for cancer therapy, stimulating factor, interferon, interleukin-2 or other lymphokine to enhance the immune system, and so forth.

2. Suture Tipping

In the process described herein one or more droplets of tipping agent may be applied to the suture either directly from a metered micropipette, or indirectly transferred from the micropipette to the suture by a carrier. The apparatus described hereinbelow can dispense micro droplets of such size as to effectively tip only that portion of the suture which is to be inserted in the shank end of a needle, typically about 0.1 inches. Preferably the droplets range in size from about 0.1 to about 0.3 microliters in volume, but the droplets can also range between about 0.4 and 1.5 microliters in volume. The tipping process is described herein with reference to applying a single droplet of tipping agent to a suture. It is contemplated, however, that multiple droplets could be applied.

Various tipping agents may be used in this process. In particular, the process described herein is especially advantageously used with a cyanoacrylate tipping agent such as described in U.S. Pat. No. 5,269,808. The cyanoacrylate is applied as a droplet of monomer whereupon it is absorbed by capillary forces into the braid structure of the suture and later hardened by curing. The preferred cyanoacrylate is available under the name LOCTITE™ Medical Device Adhesive from the Loctite Corporation of Newington, Connecticut, and comprises 99+% ethyl cyanoacrylate and small amounts of hydroquinone and organic anhydride.

Other tipping agents may be used instead of cyanoacrylate. One category of tipping agents includes solutions of tipping agents in solvents, for example, Marriotte mixture or Gould mixture. Marriotte mixture is a dipping solution composed of nylon dissolved in isopropyl alcohol. When the solvent evaporates, a solid plastic remains to adhere the filaments. Gould mixture is a solution of nylon in methanol. Other tipping solutions may be used, such as copolymers of lactic and glycolic acid dissolved in xylene or toluene, described in U.S. Pat. No. 3,736,646. U.S. Pat. No. 2,734,506 discloses a tipping solution of methacrylic acid ester polymers in an organic solvent such as toluene, xylene, acetone, ethyl acetate, methylethyl ketone, or naphtha. U.S. Pat. No. 3,849,185 discloses the use of an acrylic casting syrup as a tipping agent. In addition, paraffin/hexane solution has been used.

Other categories of substances useful in the present process are adhesives such as epoxy adhesives, adhesives cured by ultraviolet (U.V.) radiation, or adhesives which can be cured with, for example, curing accelerators.

Water or another suitable liquid may be used as a tipping agent, provided that it is frozen for a duration of time sufficient to allow the frozen portion of the suture to be cut and inserted into the needle.

Yet another category of materials which may be useful as a tipping agent are low melting point substances such as paraffin, resin, waxes, and the like which are applied as a heated liquid and later stiffened by cooling below the melting point.

Tipping agents should be bio-compatible, and may also be bioabsorbable. Cyanoacrylate is the preferred tipping agent for use in the process described herein because it is effective when used on sutures previously coated with lubricants and, under certain ambient conditions, it hardens almost instantly. The last mentioned feature, quick hardening, has often made cyanoacrylate difficult to work with. Surprisingly, a supply of cyanoacrylate monomer sufficient for several hundred applications may be stored in a conventional metered micropipette without premature hardening under most common ambient conditions. Under conditions of high humidity, which catalyzes the polymerization of cyanoacrylate and which may cause premature curing, the micropipette may be surrounded with a protective atmosphere of inert gas.

3. Tipped Suture Curing

After the suture is tipped, it may be passed through a curing station to harden the tipping agent. The specific procedure used in the curing stage will depend upon the type of tipping agent used. For example, when cyanoacrylate is used as the tipping agent the curing process involves treatment with warm moist air. Table I below outlines various suitable types of curing processes applicable for the tipping agents mentioned above.

TABLE I

| Tipping Agent | Curing Agent |
| --- | --- |
| Cyanoacrylate | Warm moist air (70° C., 90–100% humidity) |
| Marriotte, Gould mixtures | Warm, dry air (80–100° C.) |
| U.V. curable adhesives | U.V. light |
| Paraffin, resins, waxes, water | Cold air (0–20° C.) Liquid Nitrogen |

4. Suture Cutting

The suture is cut at the tipped portion to create one or two tipped ends for insertion into a surgical needle.

Cutting may be accomplished by any of the methods currently employed to sever the suture. Typically a razor edge is passed laterally across the suture.

5. Post-cutting processes

After cutting the suture optionally may be sorted according to size and diameter. A method and apparatus for sorting sutures in conjunction with a tipping and cutting process and one usable within the tipping/curing method and apparatus described herein is disclosed and described in U.S application Ser. No. 08/309,705, now U.S. Pat. No. 5,540,778.

6. Needle-Suture Assembly

The tipped end of the suture is finally inserted into the hole in the shank end of the needle. Needle-suture attachment processes and apparatus are well-known in the art. A process and apparatus for needle suture attachment which can be used for both conventional sutures and microsurgical sutures and which may be used in conjunction with the tipping and curing process described herein is disclosed in U.S. application Ser. No. 08/297,202, now abandoned.

Other methods for attaching sutures to needles are described in U.S. Pat. Nos. 5,046,350; 4,922,904; 4,799,311; 4,722,384; 4,072,041; 4,060,885; 4,054,144; and 3,910,282, for example.

THE APPARATUS

Figure 1:
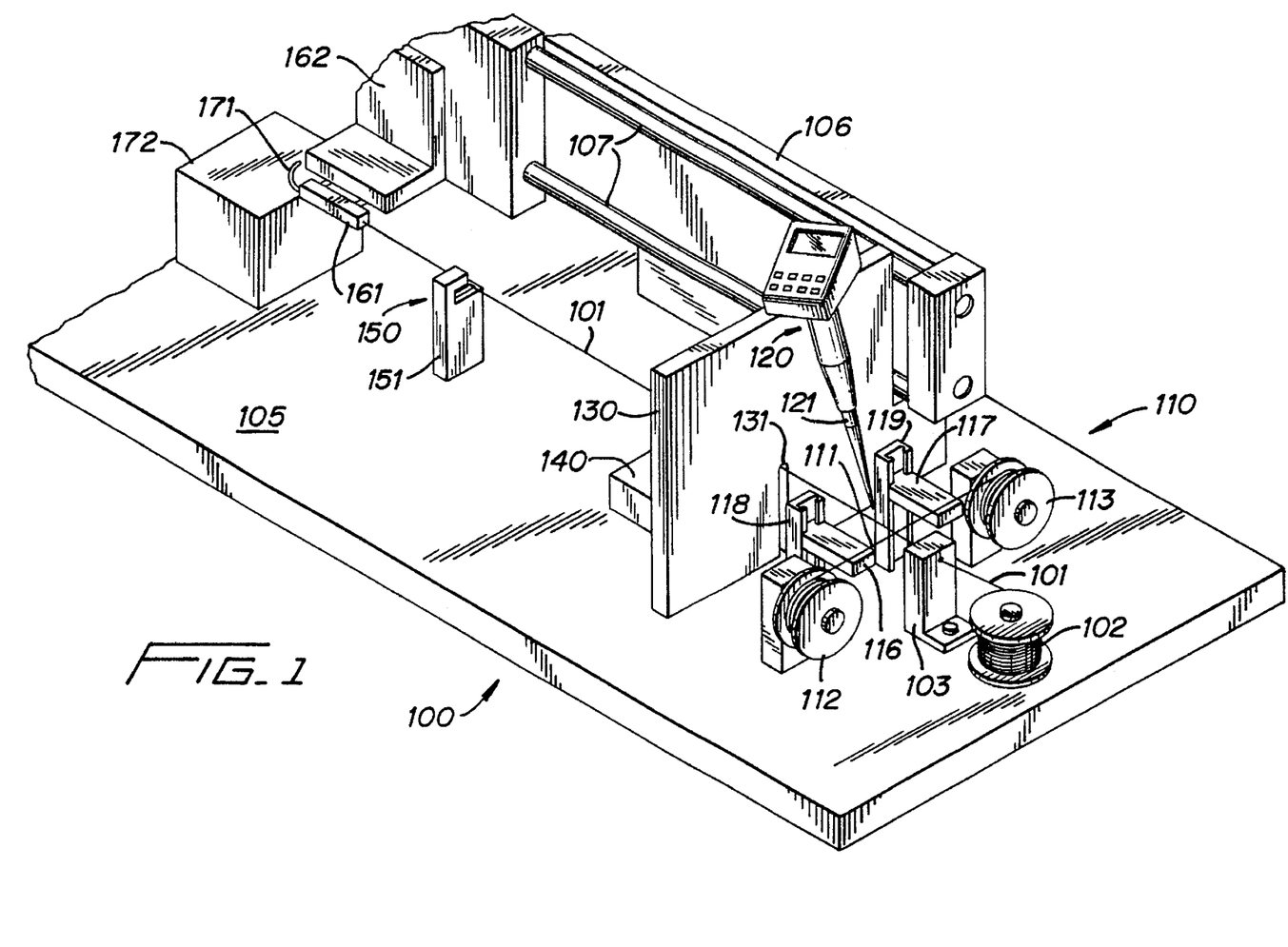
FIG. 1 is a perspective view of the apparatus.

Referring now to FIG. 1 the apparatus 100 for microtipping sutures is shown.

Base 105 supports the apparatus. Suture 101 is initially wound on suture supply spool 102 which is spring or clutch biased to maintain the suture under tension when the suture is drawn off. The suture 101 passes through aperture 104 in guide block 103 (see FIGS. 3–4), which maintains the suture in alignment. Suture 101 then passes through a tipping station which includes a positioning mechanism 110 and tipping agent dispenser 120 which is mounted to a support frame (not shown).

Figure 2:
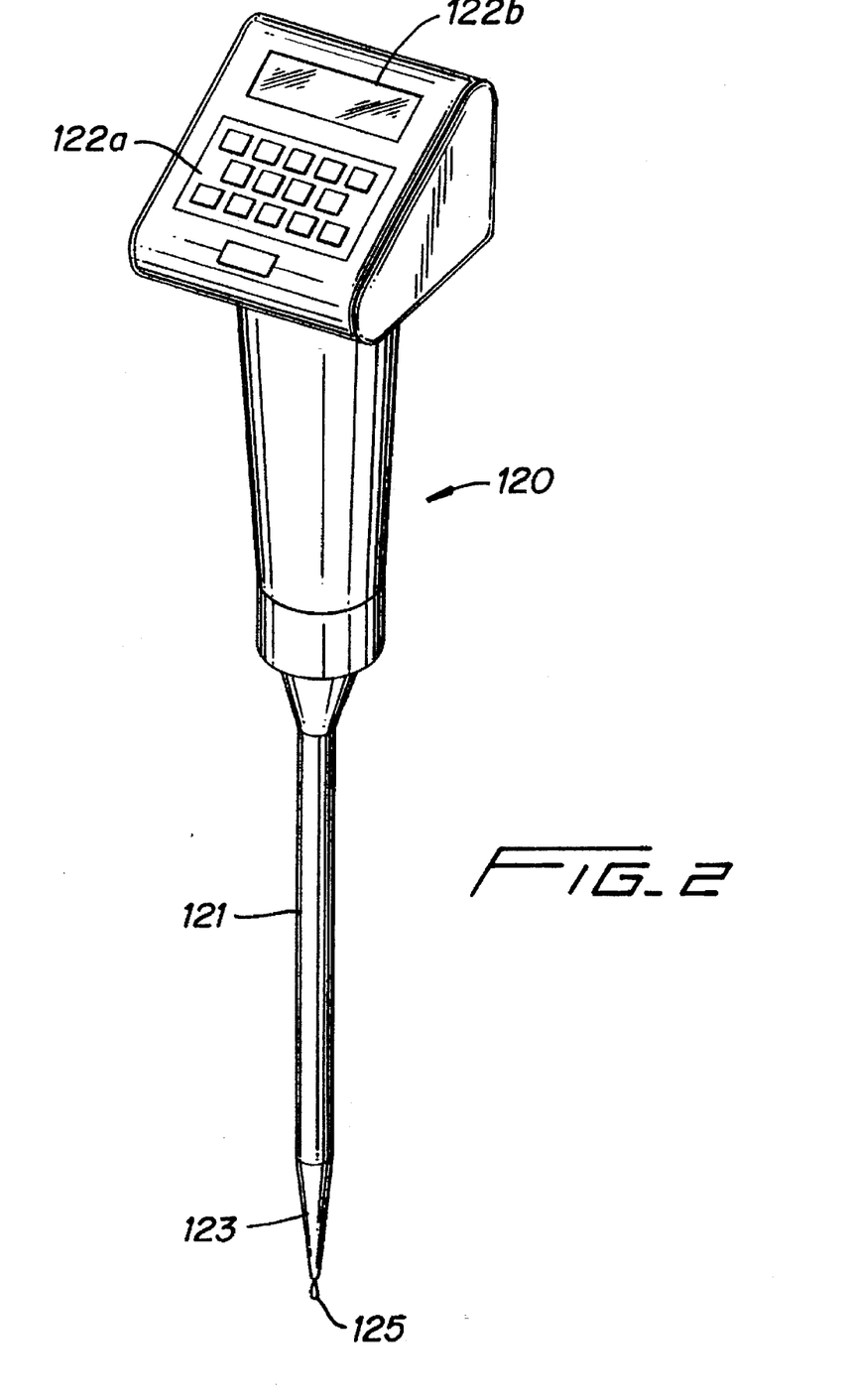
FIG. 2 is a perspective view of the metered micropipette.
Figure 3:
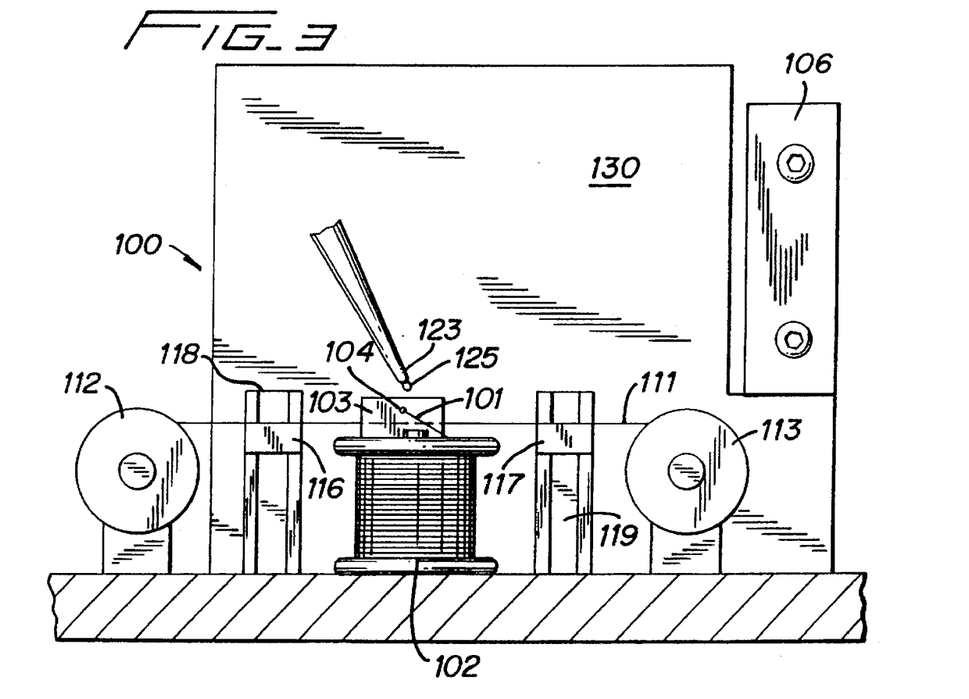
FIGS. 3 and 4 are end elevational views showing the application of tipping agent to the suture.
Figure 4:
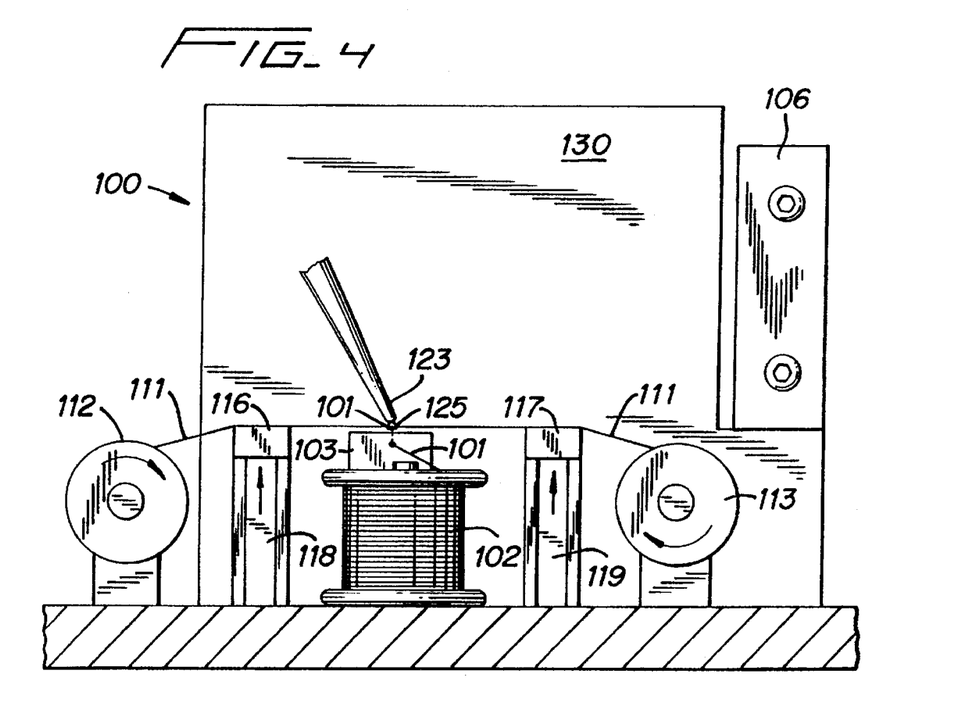
Figure 5:
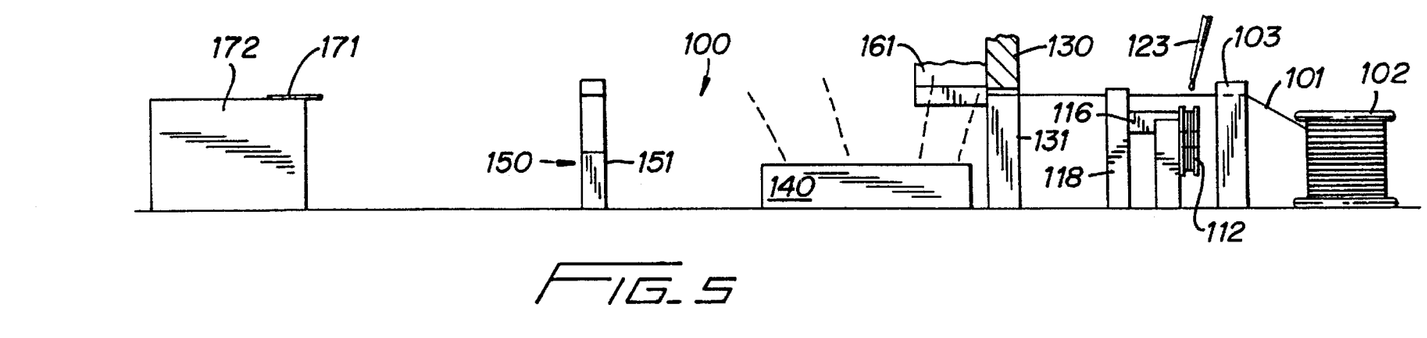
FIGS. 5, 6, and 7 are front elevational views of the stages of tipping, cutting, and needle suture assembly.
Figure 6:
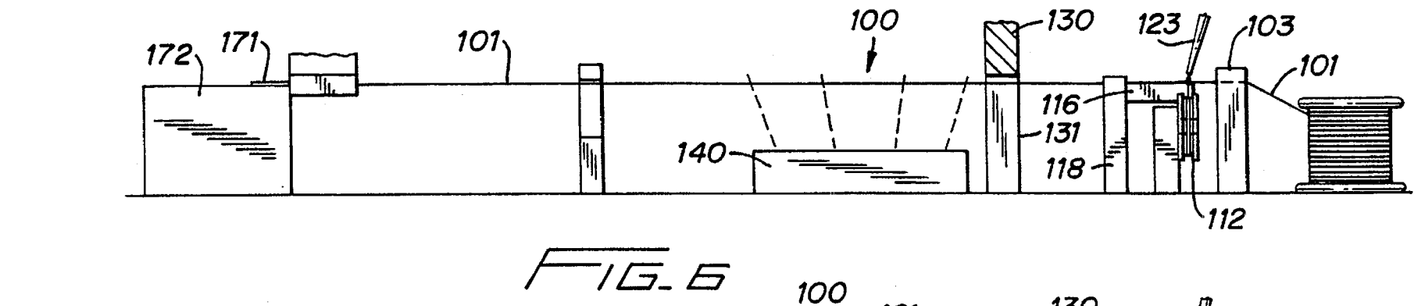
Figure 7:
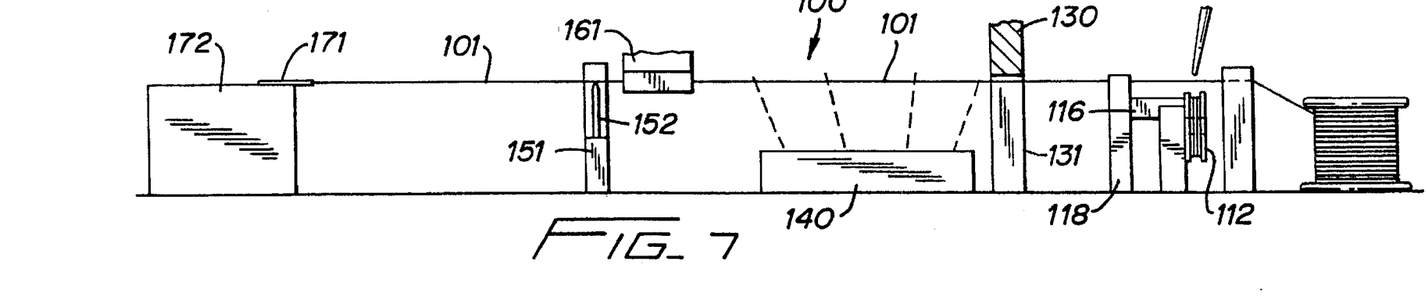

The tipping agent dispenser 120, shown in more detail in FIG. 2, is a metered micropipette which comprises an elongated cannula 121 for holding a fluid tipping agent. Such micropipettes are commercially available and known to those with skill in the art. A control panel 122 having push buttons 122a for programming and display panel 122b provides means for digitally programming the size of droplet 125 to be dispensed from the tip 123. Referring to FIGS. 1, 3, and 4, a suture positioning system 110 includes a wiping string 111 which is oriented substantially transversely to the suture 101 and which is transferred from one spool 112 to another spool 113. The wiping string 111 is positioned underneath the suture 101. Lifting platforms 116 and 117 are positioned underneath the wiping string 111 and are slidably movable along vertical tracks 118, 119, respectively, to upwardly bias the wiping string 111 which, in turn, lifts the suture 101 into contact with the droplet 125. The lifting platforms 116 and 117 may be moved manually or automatically.

When the suture 101 is lifted into contact with the droplet 125, the liquid tipping agent is absorbed into the filaments of the suture 101. The wiping string 111, which is in contact with the suture 101, is then moved linearly from one to the other of spools 112 and 113. Wiping string 111 is also preferably a multifilament string which wicks away any excess tipping agent from the suture 101, although it is contemplated that wiping string 111 may be a monofilament or other material. The excess tipping agent is wiped away by the linear movement of the wiping string 111. The tipping agent spreads out and wets a short portion of the suture, the amount of suture wetted being dependent upon the size of the droplet 125, and the wiping action of string 111. Tipping agent penetrates the suture by capillary action.

After the tipping agent has been applied, lifting platforms 116, 117 are lowered to remove wiping string 111 from contact with suture 101. The suture is then advanced until the tipped portion passes through opening 131 in shield plate 130 (see FIG. 1).

Next, the tipped suture portion passes through a curing station 140. Curing station 140 may be nothing more than exposure to ambient air, if that is sufficient to cure the tipping agent. Alternatively, the curing station may provide other suitable conditions for curing the tipping agent. In one embodiment, curing station 140 includes a blower 141 where cyanoacrylate tipping agent is used. Blower 141 may be connected to a source of warm moist air. The source of warm, moist air can comprise a column containing heated water through which air is bubbled. The temperature and humidity of the air may be chosen so as to achieve an optimum cure rate for the cyanoacrylate adhesive. Typically a temperature of 70° C. and a relative humidity of 70%–100% are sufficient. When the portion of the suture to which a tipping agent has been applied passes through the stream of warm, moist air, movement of the suture 101 may temporarily be halted to permit more contact time with the warm moist air. Curing station 140 alternatively can provide heat, radiation, etc., depending upon the curing characteristics of the particular tipping agent used.

A suture clamp 161 preferably is affixed to mounting frame 162, which is slidably mounted to longitudinally extending rails 107. Rails 107 are mounted along backframe 106. Movement of the suture 101 through the apparatus is effected by suture clamp 161, which grasps the suture in proximity to the previously tipped and cut end of the suture such that at least the amount of suture inserted into the barrel end of the needle distally extends beyond the edge of the clamp 161. The suture is pulled under tension. Preferably, a second clamp may be employed, the two clamps alternately pulling the suture 101 then moving back to secure and pull the next section of suture. An example of such an arrangement is described in U.S. application Ser. No. 08/309,705. A needle 171 is mounted to a needle support 172 at needle suture assembly station 170. The tipped end portion of suture 101 which extends distally from clamp 161 is inserted into the opening in the barrel end of needle 171, and the needle is then crimped by an appropriate crimping device (not shown). One suitable device is described in U.S. Pat. No. 5,350,373.

The suture 101 also passes through a cutting station 150 which may include a frame 151 having a knife blade 152 slidably mounted therein. The suture 101 is positioned such that the suture is cut at the portion having the cured tipping agent to create the tipped suture end. As will be appreciated, the clamp(s) 161 grasp the tipped suture adjacent cutting station 150 during cutting of the tipped suture portion to support the suture for cutting and to position the tipped suture end adjacent the clamp for insertion into the needle barrel end.

Figure 8:
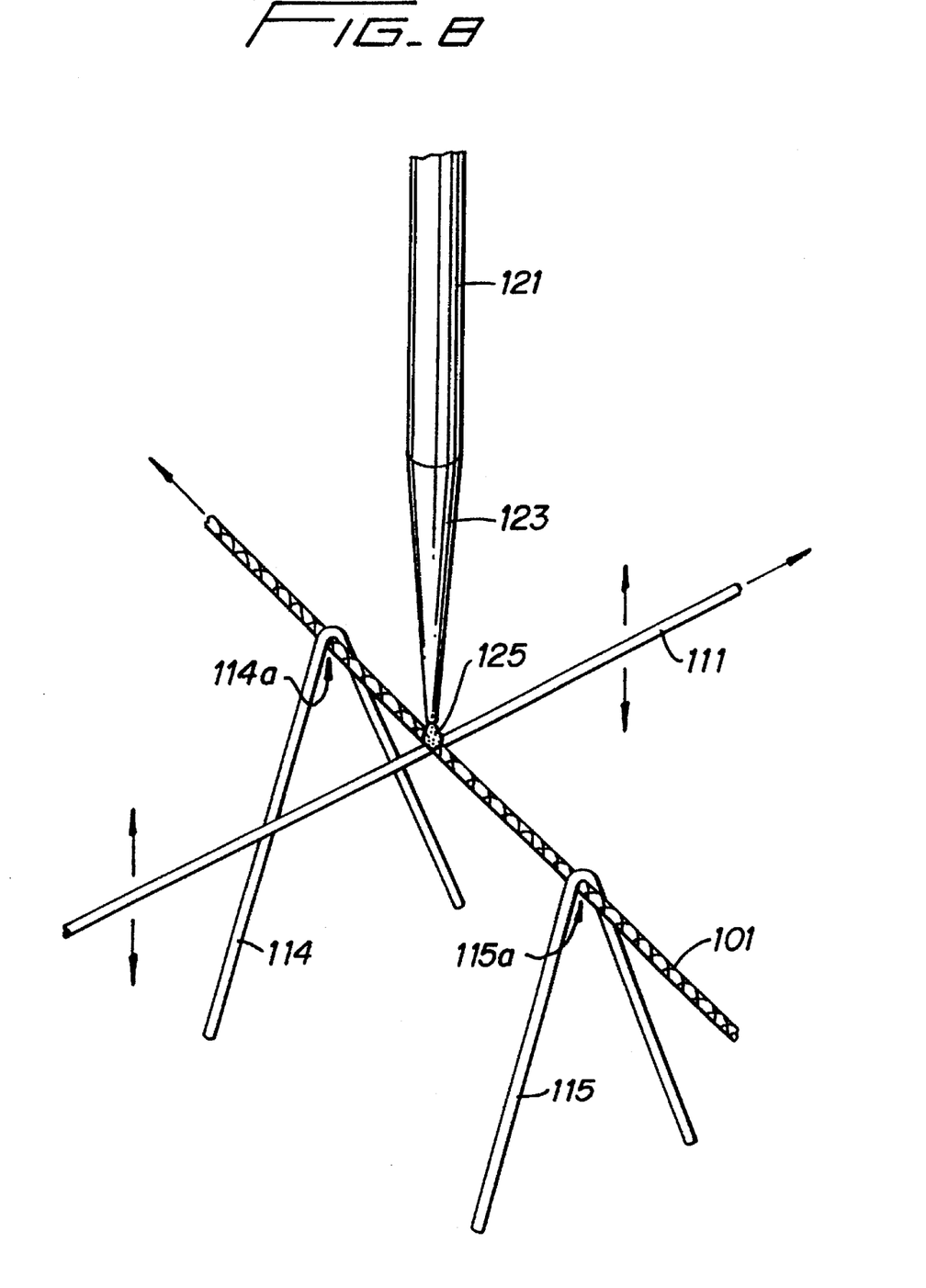
FIG. 8 is a perspective view of a wire guide system for suture alignment.

Referring now to FIG. 8 a preferred option is to additionally employ wire guides for orienting the suture in the proper position for tipping. For example, in addition to the components of the tipping station described above, it is advantageous to include inverted V-shaped guides 114 and 115 distal and proximal to the tip 123 of the tipping agent dispenser. When the suture 101 is moved upward by lifting string 111, suture 101 enters apex regions 114a and 115a which orient the suture in lateral alignment with tip 123 for precise deposition of droplet 125 onto the suture 101.

Figure 9:
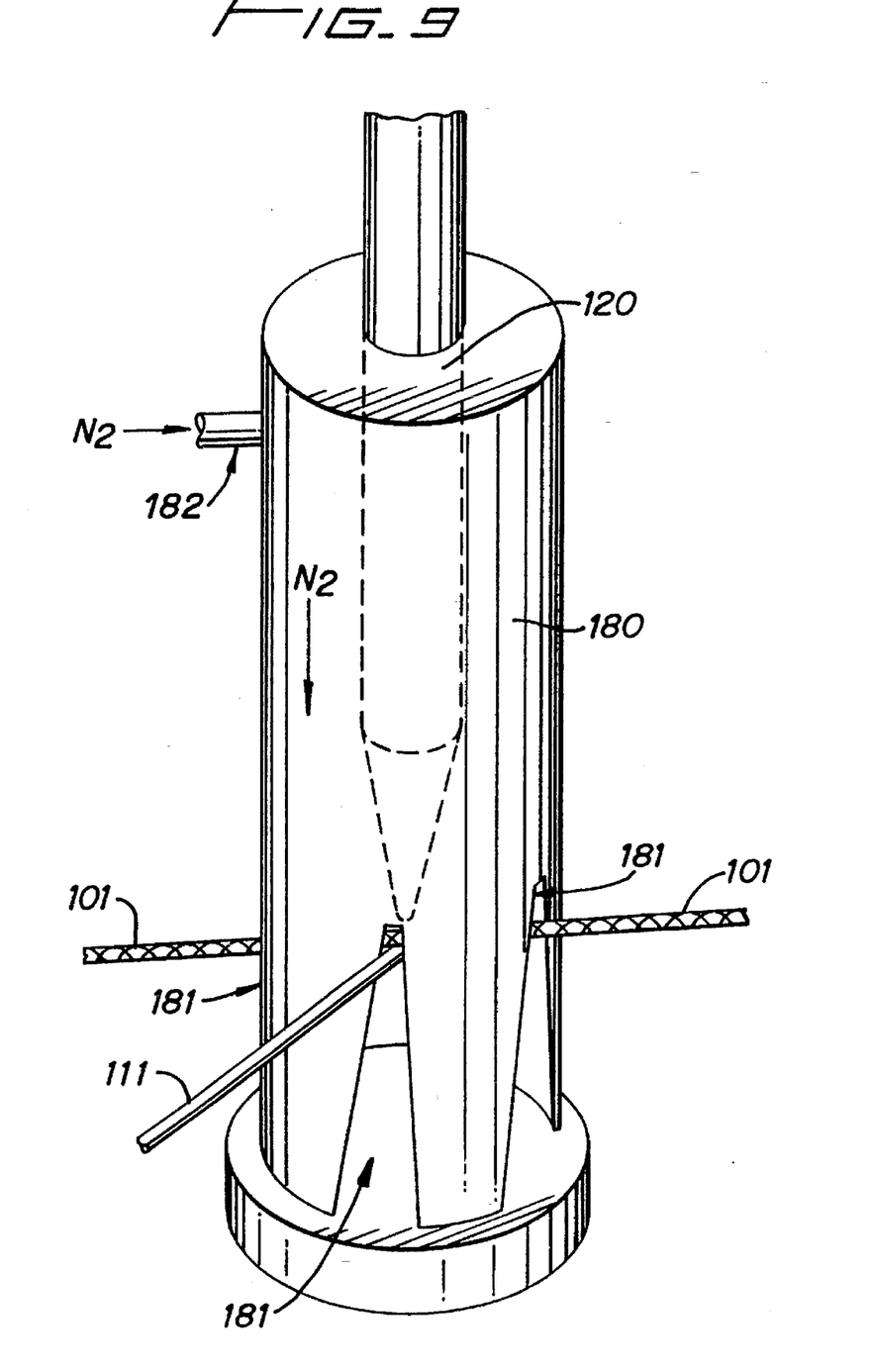
FIG. 9 is a perspective view of a collar for maintaining a controlled atmosphere.

Referring now to FIG. 9 an alternative embodiment of the apparatus is shown wherein the tipping agent dispenser 120 is surrounded by a collar 180 having an inlet 182 and outlet slots 181. Elongated cannula 121 is disposed through collar 180, the joint between them being sufficiently sealed to prevent outlet of considerable gas therebetween. Suture 101 and lifting string 111 are disposed crosswise through slots 181 such that their crossing point is oriented with the tip 123 of the cannula 12 (see FIG. 2). A substance inert to the tipping agent is pumped through inlet 182 and surrounds the tipping area to prevent premature curing or hardening of tipping agent. Where cyanoacrylate is the tipping agent, a suitable inert gas is dry nitrogen ($N_2$). Collar 180 is especially advantageous when cyanoacrylate tipping agent is used in an environment with high ambient humidity. The nitrogen within the collar is maintained at a slightly higher pressure than the atmosphere to assure that the outflow of nitrogen from slots 181 prevents the entry of humid air therethrough.

Figure 10:
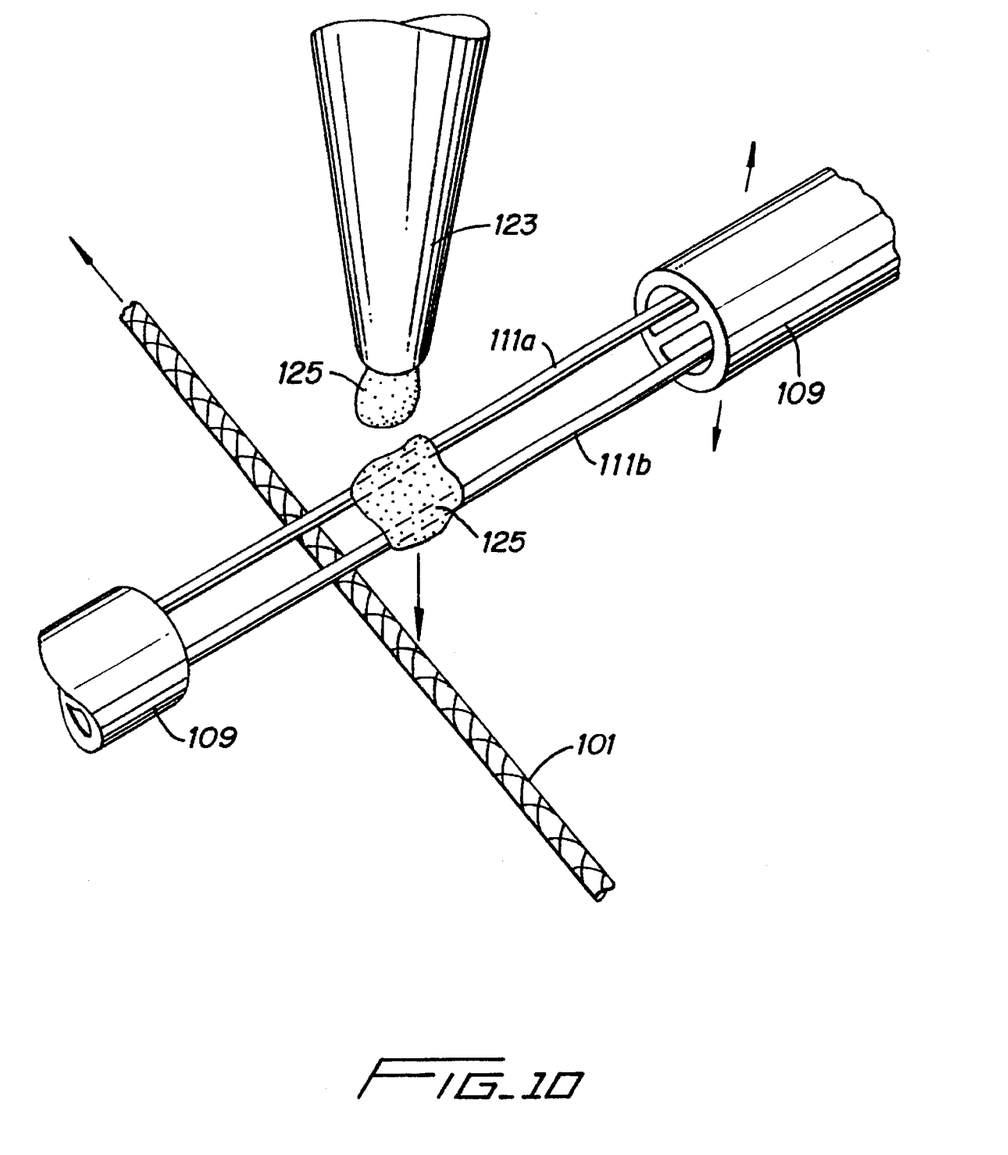
FIG. 10 is a perspective view illustrating a transport string system for applying a drop of tipping agent to a suture.

Referring to FIG. 10, another embodiment of the invention is shown wherein multifilament suture 101 is longitudinally passed underneath a pair of transverse strings 111a and 111b. Transverse strings 111a and 111b are substantially parallel to each other and spaced apart from about 0.01 to about 0.10 inches from each other. Strings 111a, 111b are oriented by a guide such as a bifurcated tubular guide 109 so that they pass underneath the tip 123 of the tipping agent dispenser 120. Strings 111a, 111b receive a droplet 125 of tipping agent and suspend the drop between them. The transverse strings 111a and 111b are preferably monofilament strings of about 0.006 inches in diameter which do not absorb the tipping agent. Transverse strings 111a and 111b are spaced and configured to hold a droplet of tipping agent liquid on and between them and transport the drop to suture 101. As indicated by direction arrows in FIG. 10, the transverse carrier strings 111a and 111b and the guide tube 109 are vertically movable. As a metered microdroplet of tipping agent 125 is deposited at tip 123 of the dispenser 120, carrier strings 111a and 111b are moved upward to catch the droplet 125 which is then held between them. The droplet size and surface tension and viscosity prevent it from falling through between the transverse carrier strings 111a and 111b. Next, the strings 111a and 111b are lowered to contact the droplet 125 with suture 101. Because the suture 101 is a multifilament suture having many interstices between its fibers and strands, it possesses a capillary force which draws the droplet 125 off the carrier strings 111a and 111b so that the droplet is absorbed into the suture filaments. Carrier strings 111a and 111b can also be moved along their own longitudinal axes so as to adjust the position of droplet 125 laterally with respect to suture 101. Thus, exact alignment of suture 101 with tip 123 of the dispenser, although preferred, is not critical. Indeed, the dispenser can be located somewhat remote from suture 101, with the carrier strings transporting the droplet of tipping agent to suture 101.

Figure 11:
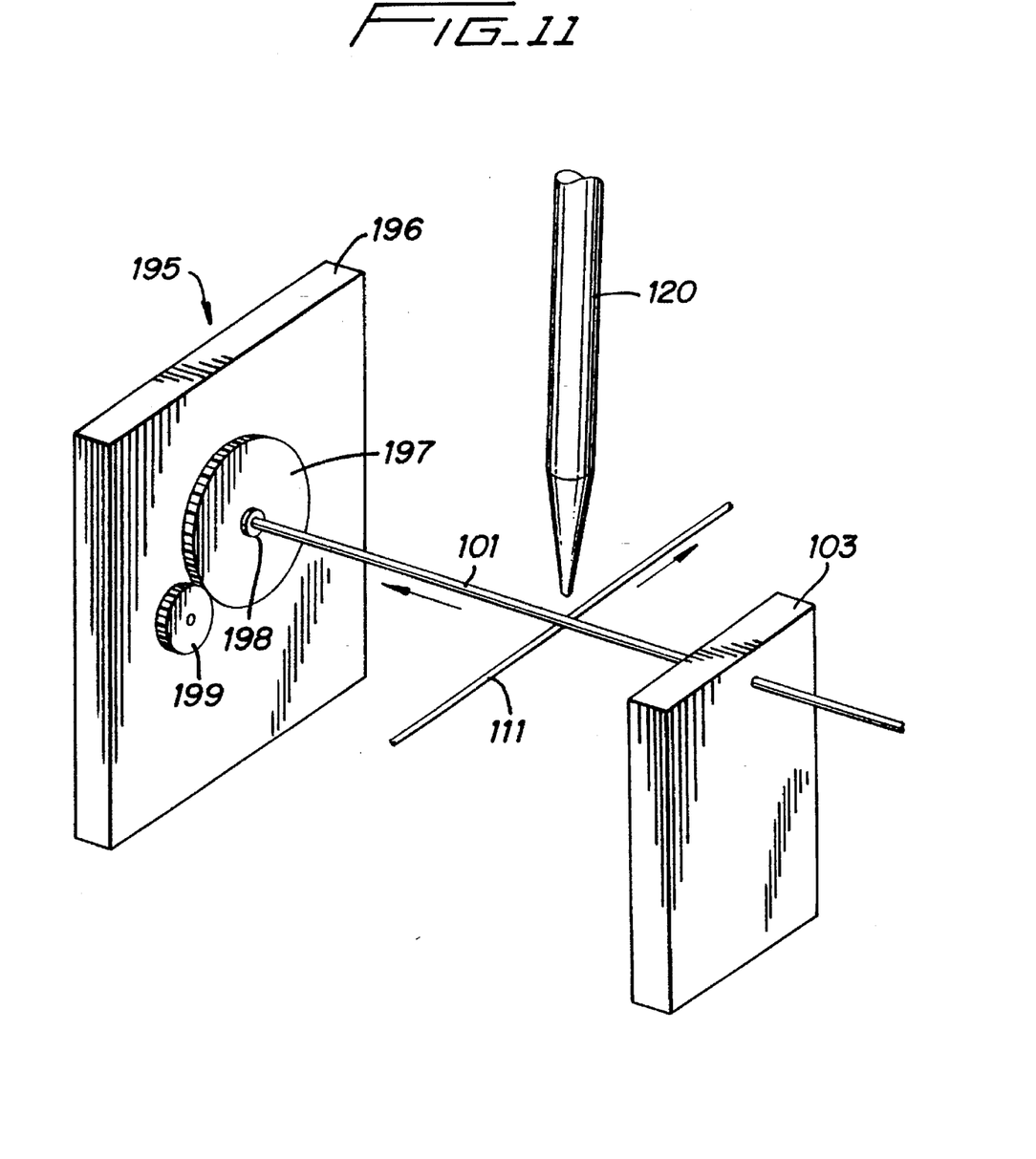
FIG. 11 is a perspective view of a suture tipping device including structure to twist the suture as tipping agent is applied to the suture.

Referring to FIG. 11, in yet another embodiment the present apparatus may include a suture twister to insure that the tipping agent wets the entire circumference of the suture portion to be tipped. As shown in FIG. 11, the suture twister 195 includes a frame 196, a disk 197 rotatably mounted on the frame 196, a suture gripping clamp 198 mounted to the disk 197, and a disk turning gear 199 rotatably mounted on the frame 196. A second suture gripping clamp 198 (not shown) is mounted to guide block 103. Both the disk 197 and gear 199 have peripheral teeth which are engaged such that rotation of gear 199 causes rotation of disk 197.

To effect twisting of suture 101, suture gripping clamps 198 are tightened and gear 199 is rotated either manually or by a motor to effect turning of the disk 197. This causes the suture 101 to twist. The disk 197 will have to be turned more than one complete rotation to result in a complete rotation of the suture at the portion which is being tipped. The suture 101 may be contacted with the droplet from dispenser 120 while twisting is being performed. After the tipping agent is absorbed, disk 197 is rotated back into its original position to untwist the suture and clamps 198 are released to permit passage of the suture to the other stations of the apparatus.

The cut, tipped suture is inserted into a channel or drilled hole of a needle and the needle is swaged or crimped to attach the suture to the needle.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

As used in the claims:

"suture transport means" refers to the slidable suture clamp and equivalent structures;

"means for contacting the suture and the drop of tipping agent" refers alternatively to transverse string 111, or strings 111a and 111b, and their structural equivalents;

"means for biasing the absorbent string" refers to the pair of lifting platforms 116 and 117 which are slidably mounted to vertical tracks 118 and 119;

"curing means" refers to the device 140 which may alternatively signify a blower of warm, moist air, warm, dry air, cold air, an ultraviolet lamp, a dispenser of accelerator, or a dispenser of liquid nitrogen, or any equivalent structure suitable for curing the tipping agent being used;

"twisting means" refers to suture twister 185.

What is claimed is:

1. A method for tipping a surgical suture comprising:

a) drawing a multifilament surgical suture under tension from a suture supply;

b) dispensing a drop of liquid tipping agent;

c) contacting a portion of the suture with the drop; and d) twisting the suture and absorbing the tipping agent into the suture to create a tipped portion of the suture.

2. The method of claim 1 wherein the step of contacting the suture portion and the drop comprises providing an elongated member oriented substantially transverse to the linear orientation of the surgical suture, positioning the elongated member such that the suture portion is between the elongated member and the drop of tipping agent, and moving the elongated member towards the drop to bias the suture portion to a position wherein contact between the suture portion and the drop is effected.

3. The method of claim 2 wherein the elongated member is an absorbent string.

4. The method of claim 3 further comprising the step of removing excess tipping agent from the tipped portion of the suture by moving the absorbent string in a direction along the axis of the absorbent string while the absorbent string is in contact with the tipped portion of the suture.

5. The method of claim 1 wherein the dispensing step comprises dispensing a drop of between about 0.4 and 1.5 microliters in volume.

6. The method of claim 1 further including the step of curing the tipping agent of the tipped portion of the suture.

7. The method of claim 1 wherein the dispensing step comprises dispensing a drop of cyanoacrylate monomer.

8. The method of claim 7 further including the step of curing the cyanoacrylate monomer of the tipped portion by exposing the tipped portion to air.

9. The method of claim 1 wherein the dispensing step comprises dispensing a tipping agent selected from the group consisting of a polymeric material in a solvent, an ultraviolet curable adhesive, paraffin, resin, and waxes.

10. A method for tipping a surgical suture comprising:

a) drawing a multifilament surgical suture under tension from a suture supply;

b) dispensing a drop of liquid tipping agent;

c) contacting a portion of the suture with the drop;

d) absorbing the tipping agent into the suture to create a tipped portion of the suture; and e) curing the tipping agent of the tipped portion of the suture;

wherein the dispensing step comprises dispensing a drop of water and the curing step comprises freezing the water.

11. The method of claim 1 further comprising the step of cutting the tipped portion of the suture to create at least one tipped end.

12. The method of claim 11 further including the steps of inserting the cut end of the suture into an aperture in a surgical needle and crimping the needle to secure the suture thereto.

13. The method of claim 1 wherein the step of contacting a portion of the suture with the drop comprises applying the drop to a carrier and then moving the carrier to bring the drop into contact with a portion of the suture.

14. A method for tipping a surgical suture comprising:

a) drawing a multifilament surgical suture under tension from a suture supply;

b) dispensing a drop of liquid tipping agent;

c) contacting a portion of the suture with the drop by applying the drop to at least one elongated member oriented substantially transverse to the orientation of the suture and then moving the at least one elongated member to bring the drop into contact with the portion of the suture; and d) absorbing the tipping agent into the suture to create a tipped portion of the suture.

15. The method of claim 14 wherein the step of applying the drop to the carrier comprises applying the drop to two spaced apart parallel strings oriented substantially transverse to the orientation of the suture.

16. The method of claim 1 further comprising the step of relaxing the suture after the suture has been twisted and the tipping agent has been at least partially absorbed.

17. A method for tipping a surgical suture comprising;

a) providing a length of multifilament surgical suture under tension:

b) dispensing a drop of liquid tipping agent;

c) providing an elongated member oriented substantially transverse to the linear orientation of the surgical suture;

d) positioning the elongated member such that the suture portion is between the elongated member and the drop of tipping agent;

e) moving the elongated member towards the drop to bias the suture portion to a position wherein contact between the suture portion and the drop is effected; and f) absorbing the tipping agent into the suture to create a tipped portion of the suture.

18. The method of claim 17 wherein the elongated member is an absorbent string.

19. The method of claim 17 further comprising the step of removing excess tipping agent from the tipped portion of the suture by moving the absorbent string in a direction along the axis of the absorbent string while the absorbent string is in contact with the tipped portion of the suture.

20. The method of claim 17 wherein the dispensing step comprises dispensing a drop of between about 0.4 and 1.5 microliters in volume.

21. The method of claim 17 further including the step of curing the tipping agent of the tipped portion of the suture.

22. The method of claim 17 wherein the dispensing step comprises dispensing a drop of cyanoacrylate monomer.

23. The method of claim 22 further including the step of curing the cyanoacrylate monomer of the tipped portion by exposing the tipped portion to air.

24. The method of claim 17 wherein the dispensing step comprises dispensing a tippling agent selected from the group consisting of a polymeric material in a solvent, an ultraviolet curable adhesive, paraffin, resin, and waxes.

25. The method of claim 17 further comprising the step of cutting the tipped portion of the suture to create at least one tipped end.

26. The method of claim 25 further including the steps of inserting the cut end of the suture into an aperture in a surgical needle and crimping the needle to secure the suture thereto.

27. The method of claim 17 wherein the elongated member is moved toward the drop by translational motion.

* * * * *